United States Patent [19]

Lee

[11] Patent Number: 4,482,727
[45] Date of Patent: Nov. 13, 1984

[54] CERTAIN 1,3-CYCLOHEXANEDIONE ADDUCTS OF SUBSTITUTED PHENOXYPHENOXYPROPIONIC ACIDS AND THEIR USE AS AN HERBICIDE

[75] Inventor: David L. Lee, Martinez, Calif.

[73] Assignee: Stauffer Chemical Company, Westport, Conn.

[21] Appl. No.: 510,141

[22] Filed: Jul. 1, 1983

[51] Int. Cl.$^3$ .................. C07D 309/32; C07C 49/517
[52] U.S. Cl. .................................. 549/291; 568/329; 71/123; 71/88
[58] Field of Search ........................ 549/291; 568/329

[56] References Cited

PUBLICATIONS

Chemical Abstracts (1977) 86:189318z.
Chemical Abstracts (1976) 84:175144m.

Primary Examiner—Norma S. Milestone
Attorney, Agent, or Firm—Edwin H. Baker

[57] ABSTRACT

Compounds having the structural formula

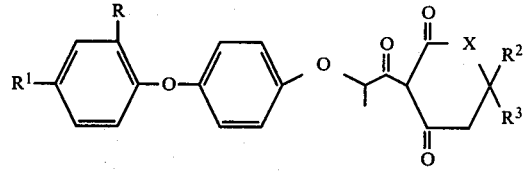

wherein R is hydrogen or halogen, $R^1$ is halogen, $R^2$ is hydrogen or $C_1$–$C_4$ alkyl, $R^3$ is hydrogen or $C_1$–$C_4$ alkyl, and X is oxygen or methylene useful as post-emergent herbicides against annual and perennial grasses.

6 Claims, No Drawings

CERTAIN 1,3-CYCLOHEXANEDIONE ADDUCTS OF SUBSTITUTED PHENOXYPHENOXYPROPIONIC ACIDS AND THEIR USE AS AN HERBICIDE

BACKGROUND OF THE INVENTION

The present invention relates to certain 1,3-cyclohexanedione adducts of substituted phenoxyphenoxypropionic acids which are particularly useful as post-emergent herbicides against annual and perennial grasses.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way.

There are a number of different types of herbicides presently sold commercially, and these fall into two general categories. The categories are pre-emergence and post-emergence herbicides. The pre-emergence herbicides are normally incorporated into or applied to the soil prior to the emergence of the weed plants from the soil, and the post-emergence herbicides are normally applied to plant surfaces after emergence of the weeds or other unwanted plants from the soil.

THE PRIOR ART

The prior art is replete with examples of propionic acid-type compounds which have been disclosed to be herbicidally effective against grasses in particular, as compared to broad leaf weed pests. Examples of such prior art references include U.S. Pat. Nos. 4,200,587 and 4,325,729, both of which disclose propionic acid derivatives as being effective herbicides against grasses.

Efforts are constantly being made, however, to find compounds which are equal to or greater in effectiveness than presently existing compounds, or which are more economical to produce.

DESCRIPTION OF THE INVENTION

This invention relates to certain novel 2-[(substituted phenoxy)phenoxypropionyl]-1,3-cyclohexanediones as herbicides. The compounds of this invention have the following structural formula

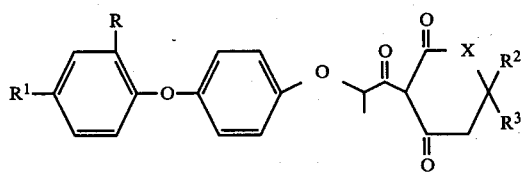

wherein:
R is hydrogen or halogen, preferably chlorine;
$R^1$ is halogen, preferably chlorine or trifluoromethyl;
$R^2$ is hydrogen or $C_1$–$C_4$ alkyl, preferably methyl,
$R^3$ is hydrogen or $C_1$–$C_4$ alkyl, preferably methyl; and
X is oxygen or methylene.

The compounds of this invention can have the following three structural formulae because of tautomerism:

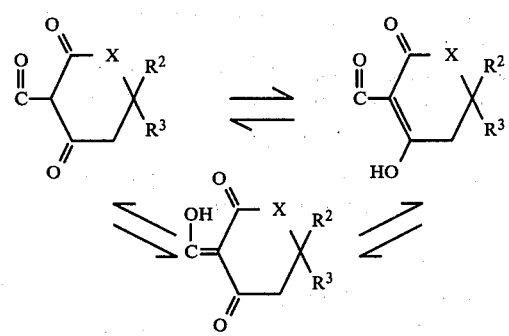

wherein $R^2$ and $R^3$ are as defined above and the moiety of the molecule attached to the carbonyl groups for the three forms shown is:

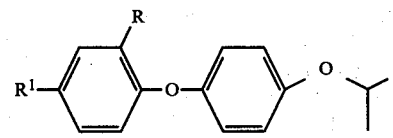

In the above description of the compounds of this invention alkyl and alkoxy include both straight and branched configurations; for example, methyl, ethyl, n-propyl, isopropyl, n-butyl, sec-butyl, isobutyl, and tert-butyl. Halogen means chlorine, bromine, iodine and fluorine.

The compounds of this invention are active herbicides of a general type. That is, they are herbicidally effective against a wide range of plant species. The method of controlling undesirable vegetation of the present invention comprises applying an herbicidally effective amount of the above-described compounds to the area where control is desired.

The compounds of the present invention can be prepared by the following general method.

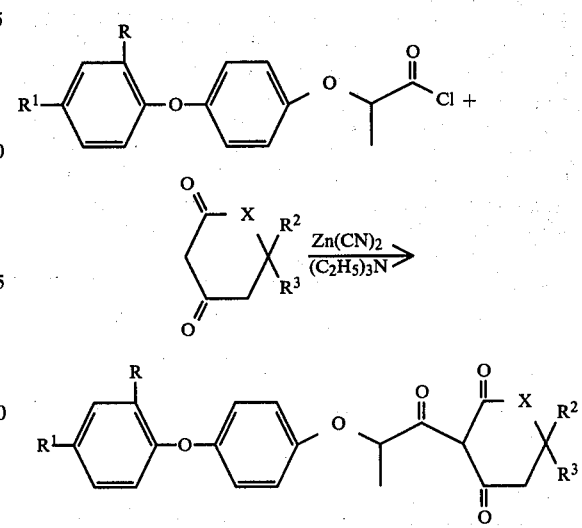

Generally, equimolar amounts of the dione and the acid chloride are used, along with a slight molar excess of zinc cyanide. The two reactants and the zinc cyanide are combined in a solvent such as acetonitrile. A slight mole excess of triethylamine is slowly added to the reaction mixture. The mixture is stirred at reflux for one hour.

The reaction product is worked up by conventional techniques.

The following example teaches the synthesis of a representative compound of this invention.

EXAMPLE I

2-[2-(4-(2,4-dichlorophenoxy)phenoxy)propionyl]-1,3-cyclohexanedione

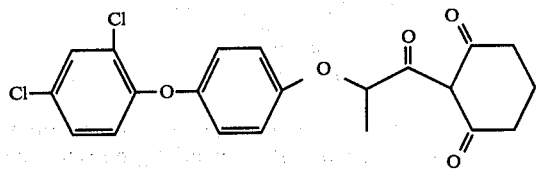

To a solution of the acid chloride (10 grams (g), 0.0306 mole) in 100 milliliter (ml) of dry acetonitrile was added zinc cyanide (4.7 g, 0.04 mole) in one lot. After stirring for 15 minutes at room temperature, cyclohexane-1,3-dione (4.5 g, 0.04 mole) was added in one lot following by the dropwise addition of triethylamine (5.05 g, 0.05 mole) over a period of 5 minutes. After the initial exotherm had subsided (approximately 15 minutes), the reaction mixture was heated at reflux for an additional hour. The reaction mixture was allowed to cool to room temperature, and the acetonitrile was evaporated in vacuo on a rotary evaporator. The residue solid was then digested with 2N HCl and ethyl ether. The layers were separated, and the ethereal layer was extracted with 5% $K_2CO_3$. Acidification of the basic extract afforded the crude triketone which was adulterated with a minor amount of acid that was derived from the starting acid chloride. The crude triketone was then further purified via formation of its copper complex. The crude triketone was dissolved in 1:1 hexane-ether and stirred with a 5% copper acetate solution. The blue copper complex that formed was isolated through filtration. The complex was destroyed with 6N HCl, and the acidic aqueous mixture was extracted with ether. The layers were separated, and the ethereal layer was concentrated in vacuo to afford the desired product triketone, m.p.=57°–68° C.

The following is a table of certain selected compounds that are preparable according to the procedure described hereto. Compound numbers are assigned to each compound and are used throughout the remainder of the application.

TABLE I

| Compound Number | R | $R^1$ | $R^2$ | $R^3$ | X | $N_D^{30}$ or m.p. °C. |
|---|---|---|---|---|---|---|
| 1 | Cl | $CF_3$ | H | H | $CH_2$ | thick liquid |
| 2 | Cl | Cl | H | H | $CH_2$ | 57.0–68.0 |
| 3 | Cl | Cl | H | $CH_3$ | O | semi-solid |
| 4 | Cl | Cl | $CH_3$ | $CH_3$ | $CH_2$ | semi-solid |

TABLE I-continued

| Compound Number | R | $R^1$ | $R^2$ | $R^3$ | X | $N_D^{30}$ or m.p. °C. |
|---|---|---|---|---|---|---|
| 5 | H | $CF_3$ | H | H | $CH_2$ | 86.0–90.0 |
| 6 | H | $CF_3$ | $CH_3$ | $CH_3$ | $CH_2$ | semi-solid |
| 7 | H | $CF_3$ | H | $CH_3$ | O | semi-solid |
| 8* | H | $CF_3$ | $CH_3$ | $CH_3$ | $CH_2$ | >250° |

*sodium salt of recited compound

Herbicidal Screening Tests

As previously mentioned, the herein described compounds produced in the above-described manner are phytotoxic compounds which are useful and valuable in controlling various plant species. Selected compounds of this invention were tested as herbicides in the following manner.

Pre-emergence herbicide test. On the day preceding treatment, seeds of eight different weed species are planted in loamy sand soil in individual rows using one species per row across the width of a flat. The seeds used are green foxtail (FT) (*Setaria viridis*), watergrass (WG) (*Echinochloa crusgalli*), wild oat (WO) (*Avena fatua*), annual morningglory (AMG) (*Ipomoea lacunosa*), velvetleaf (VL) (*Abutilon theophrasti*), Indian mustard (MD) (*Brassica juncea*), curly dock (CD) (*Rumex crispus*), and yellow nutsedge (YNG) (*Cyperus esculentus*). Ample seeds are planted to give about 20 to 40 seedlings per row, after emergence, depending upon the size of the plants.

Using an analytical balance, 600 milligrams (mg) of the compound to be tested are weighed out on a piece of glassine weighing paper. The paper and compound are placed in a 60 milliliter (ml) wide-mouth clear bottle and dissolved in 45 ml of acetone or substituted solvent. Eighteen ml of this solution are transferred to a 60 ml wide-mouth clear bottle and diluted with 22 ml of a water and acetone mixture (19:1) containing enough polyoxyethylene sorbitan monolaurate emulsifier to give a final solution of 0.5% (v/v). The solution is then sprayed on a seeded flat on a linear spray table calibrated to deliver 80 gallons per acre (748 L/ha). The application rate is 4 lb/acre (4.48 Kg/ha).

After treatment, the flats are placed in the greenhouse at a temperature of 70° to 80° F. and watered by sprinkling. Two weeks after treatment, the degree of injury or control is determined by comparison with untreated check plants of the same age. The injury rating from 0 to 100% is recorded for each species as percent control with 0% representing no injury and 100% representing complete control.

The results of the tests are shown in the following Table II.

Post-Emergence Herbicide Test: This test is conducted in an identical manner to the testing procedure for the pre-emergence herbicide test, except the seeds of the eight different weed species are planted 10–12 days before treatment. Also, watering of the treated flats is confined to the soil surface and not to the foliage of the sprouted plants.

The results of the post-emergence herbicide test are reported in Table II.

TABLE II

Pre-Emergence Herbicidal Activity
Application Rate - 4.48 kg/ha

| Cmpd. No. | FT | WG | WO | AMG | VL | MD | CD | YNG |
|---|---|---|---|---|---|---|---|---|
| 1 | 95 | 95 | 85 | 0 | 0 | 0 | 30 | 0 |
| 2 | 100 | 100 | 20 | 0 | 0 | 0 | 0 | 0 |
| 3 | 25 | 60 | 40 | 0 | 0 | 0 | 0 | 0 |
| 4 | 100 | 90 | 80 | 0 | 0 | 0 | 90 | 0 |
| 5 | 90 | 100 | 55 | 0 | 0 | 0 | 0 | 0 |
| 6 | 100 | 100 | 50 | 0 | 0 | 0 | 90 | 0 |
| 7 | 95 | 100 | 50 | 0 | 0 | 0 | 0 | 0 |
| 8 | 100 | 100 | 90 | 0 | 0 | 0 | 95 | 0 |

TABLE III

Post-Emergence Herbicidal Activity
Application Rate - 4.48 kg/ha

| Cmpd. No. | FT | WG | WO | AMG | VL | MD | CD | YNG |
|---|---|---|---|---|---|---|---|---|
| 1 | 100 | 100 | 85 | 60 | 60 | 60 | 0 | 0 |
| 2 | 50 | 90 | 20 | 0 | 0 | 20 | 0 | 0 |
| 3 | 90 | 100 | 40 | 20 | 0 | 20 | 0 | 0 |
| 4 | 10 | 10 | 20 | 0 | 0 | 20 | 0 | 0 |
| 5 | 90 | 100 | 100 | 0 | 0 | 0 | 0 | 0 |
| 6 | 100 | 100 | 40 | 0 | 0 | 0 | 0 | 0 |
| 7 | 100 | 100 | 100 | 0 | 0 | 0 | 0 | 0 |
| 8 | 95 | 80 | 75 | 0 | 0 | 0 | 0 | 0 |

The compounds of the present invention are useful as herbicides, especially as post-emergence herbicides, and can be applied in a variety of ways at various concentrations. In practice, the compounds herein defined are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds may be formulated as granules of relatively large particle size, as wettable powders, as emulsifiable concentrates, as powdery dusts, as solutions or as any of several other known types of formulations, depending upon the desired mode of application. Preferred formulations for pre-emergence herbicidal applications are wettable powders, emulsifiable concentrates and granules. These formulations may contain as little as about 0.5% to as much as about 95% or more by weight of active ingredient. A herbicidally effective amount depends upon the nature of the seeds or plants to be controlled and the rate of application varies from about 0.05 to approximately 25 pounds per acre, preferably from about 0.1 to about 10 pounds per acre.

Wettable powders are in the form of finely divided particles which disperse readily in water or other dispersants. The wettable powder is ultimately applied to the soil either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphthal, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers for granular formulations include sand, fuller's earth, bentonite clays, vermiculite, perlite and other organic or inorganic materials which absorb or which may be coated with the toxicant. Granular formulations normally are prepared to contain about 5% to about 25% of active ingredients which may include surface-active agents such as wetting agents, dispersing agents or emulsifiers; oil such as heavy aromatic naphthas, kerosene or other petroleum fractions, or vegetable oils; and/or thickeners such as dextrins, glue or synthetic resins.

Typical wetting, dispersing or emulsifying agents used in agricultural formulations include, for example, the alkyl and alkylaryl sulfonates and sulfates and their sodium salts; polyhydroxy alcohols; and other types of surface-active agents, many of which are available in commerce. The surface-active agent, when used, normally comprises from 0.1% to 15% by weight of the herbicidal composition.

Dusts, which are free-flowing admixtures of the active ingredient with finely divided solids such as talc, clays, flours and other organic and inorganic solids which act as dispersants and carriers for the toxicant, are useful formulations for soil-incorporating application.

Pastes, which are homogeneous suspensions of a finely divided solid toxicant in a liquid carrier such as water or oil, are employed for specific purposes. These formulations normally contain about 5% to about 95% of active ingredients by weight, and may also contain small amounts of a wetting, dispersing or emulsifying agent to facilitate dispersion. For application, the pastes are normally diluted and applied as a spray to the area to be affected.

Other useful formulations for herbicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to conventional methods and are distributed in the soil to a depth of at least ½ inch below the soil surface. It is not necessary that the phytotoxic compositions be admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers, pesticides and the like, used as adjuvant or in combination with any of the above-described adjuvants. Other phytotoxic compounds useful in combination with the abovedescribed compounds include, for example, 2,4-dichlorophenoxyacetic acids, 2,4,5-trichlorophenoxyacetic acid, 2-methyl-4-chlorophenoxyacetic acid and the salts, esters and amides thereof, triazine derivatives, such as 2,4-bis-(3-methoxypropylamino-6-methylthio-s-triazine, 2-chloro-4-ethylamino-6-isopropylamino-s-triazine, and 2-ethylamino-4-isopropyl-amino-6-methyl-mercapto-s-triazine; urea derivatives, such as 3-(3,5-dichlorophenyl)-1,1-dimethylurea and 3-(p-chlorophenyl)-1,1-dimethylurea; and acetamides such as N,N-diallyl-α-chloroacetamide, and the like; benzoic acids such as 3-amino-2,5-dichlorogbenaoic acid; thiocarbamates such as S-propyl N,N-dipropytlthiocarbamate, S-ethyl N,N,-dipropylthiocarbamate, S-ethyl cyclohexylethyl thiocarbamate, S-ethyl hexahydro-1H-azepine-1-carbothioate and the like; anilines such as 4-(methyl-sulfonyl)-2,6-dinitro-N,N-substituted aniline, 4-trifluoromethyl-2,6-dinitro-N,N-di-n-propyl aniline and 4-trifluoromethyl-2,6-dinitro-N-ethyl-N,N-di-n-butyl aniline. Fertilizers useful in combination with the active ingredients include, for example, ammonium nitrate, urea and superphosphate. Other useful additaments include materials in which plant organisms take root and grow such as compost, manure, humus, sand, and the like.

We claim:

1. A compound having the structural formula

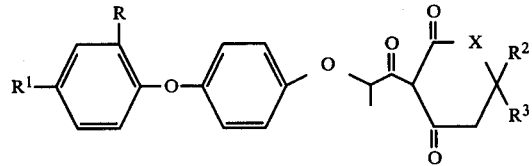

wherein R is hydrogen or halogen, $R^1$ is halogen or trifluoromethyl, $R^2$ is hydrogen or $C_1$-$C_4$ alkyl, $R^3$ is hydrogen or $C_1$-$C_4$ alkyl and X is oxygen or methylene.

2. The compound of claim 1 wherein R is chlorine, $R^1$ is trifluoromethyl, $R^2$ is hydrogen, $R^3$ is hydrogen and X is methylene.

3. The compound of claim 1 wherein R is chlorine, $R^1$ is chlorine, $R^2$ is hydrogen, $R^3$ is methyl and X is oxygen.

4. The compound of claim 1 wherein R is hydrogen, $R^1$ is trifluoromethyl, $R^2$ is hydrogen, $R^3$ is hydrogen, and X is methylene.

5. The compound of claim 1 wherein R is hydrogen, $R^1$ is trifluoromethyl, $R^2$ is hydrogen, $R^3$ is methyl, and X is oxygen.

6. The compound of claim 1 wherein R is hydrogen, $R^1$ is trifluoromethyl, $R^2$ is methyl, $R^3$ is methyl, and X is methylene.

* * * * *